US012337160B1

(12) United States Patent  
Hee-Hanson et al.

(10) Patent No.: US 12,337,160 B1  
(45) Date of Patent: Jun. 24, 2025

(54) MEDICAMENT DELIVERY DEVICE

(71) Applicant: Genzyme Corporation, Cambridge, MA (US)

(72) Inventors: Alexander Hee-Hanson, Melbourn (GB); Michael Parrott, Melbourn (GB)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 18/640,600

(22) Filed: Apr. 19, 2024

(51) Int. Cl.
*A61M 5/32* (2006.01)
*A61M 5/315* (2006.01)

(52) U.S. Cl.
CPC ...... *A61M 5/3287* (2013.01); *A61M 5/31571* (2013.01); *A61M 5/3158* (2013.01); *A61M 5/3202* (2013.01)

(58) Field of Classification Search
CPC ............ A61M 5/31511; A61M 5/3287; A61M 5/3158; A61M 3/315; A61M 5/31571; A61M 5/31501; A61M 5/5013; A61M 5/31585; A61M 5/31576; A61M 5/20; A61M 5/2033; A61M 5/24; A61M 5/2422; A61M 5/31565; A61M 5/31566; A61M 5/31578; A61M 5/3159; A61M 5/32; A61M 5/3202; A61M 2005/2006; A61M 2005/2013; A61M 2005/206;
(Continued)

(56) References Cited

U.S. PATENT DOCUMENTS

| | | | |
|---|---|---|---|
| 2,522,961 | A | 9/1950 | William |
| 2,633,267 | A | 3/1953 | Lebus |
| 3,886,513 | A | 5/1975 | Smith et al. |

(Continued)

FOREIGN PATENT DOCUMENTS

| | | |
|---|---|---|
| DE | 3921747 A1 | 1/1991 |
| EP | 3501577 A1 | 6/2019 |

(Continued)

OTHER PUBLICATIONS

Needle-based injection systems for medical use requirements and test methods, Part 1: Needle injection systems, ISO 11608-1:2014(E), Third Edition, Switzerland, ISO, Dec. 15, 2014, pp. 1-13.

(Continued)

*Primary Examiner* — Shefali D Patel  
*Assistant Examiner* — Nidah Hussain  
(74) *Attorney, Agent, or Firm* — Fish & Richardson P.C.

(57) ABSTRACT

A medicament delivery device has an actuation member which is movable relative to a body. The actuation member has a flexible arm comprising an engagement surface. The device has a contoured surface. When the actuation member is in a first position the engagement surface engages the contoured surface. When the actuation member moves to a second position, the flexible arm is deflected radially by the engagement of the engagement surface with the contoured surface. The device further has a blocking member. The blocking member has a proximal portion which engages the flexible arm when the blocking member is in an extended position for preventing the flexible arm from being deflected radially and moving distally. The blocking member is movable relative to the body to disengage the proximal portion from the flexible arm.

30 Claims, 7 Drawing Sheets

(58) Field of Classification Search
CPC .... A61M 2005/2073; A61M 2005/208; A61M 2005/2403; A61M 2005/31508
USPC ........................................................ 604/506
See application file for complete search history.

(56) References Cited

U.S. PATENT DOCUMENTS

| | | |
|---|---|---|
| 4,801,295 A | 1/1989 | Spencer |
| 5,045,062 A | 9/1991 | Henson |
| 5,176,275 A | 1/1993 | Bowie |
| 5,328,484 A | 7/1994 | Somers et al. |
| 5,396,051 A | 3/1995 | Kuhn et al. |
| 5,478,316 A | 12/1995 | Bitdinger et al. |
| 5,505,324 A | 4/1996 | Danico |
| 5,505,706 A | 4/1996 | Maus et al. |
| 5,536,917 A | 7/1996 | Suppelsa et al. |
| 5,622,274 A | 4/1997 | Bright |
| 5,738,658 A | 4/1998 | Maus et al. |
| 5,984,899 A | 11/1999 | D'Alessio et al. |
| 6,080,461 A | 6/2000 | Wozniak et al. |
| 6,394,985 B1 | 5/2002 | Lin |
| 7,762,981 B2 | 7/2010 | Dacquay et al. |
| 7,887,506 B1 | 2/2011 | Smolyarov et al. |
| 7,918,824 B2 | 4/2011 | Bishop et al. |
| 8,133,198 B2 | 3/2012 | Neer |
| 8,409,138 B2 | 4/2013 | James et al. |
| 8,734,394 B2 | 5/2014 | Adams et al. |
| 9,044,553 B2 | 6/2015 | James et al. |
| 9,402,957 B2 | 8/2016 | Adams et al. |
| 9,872,961 B2 | 1/2018 | Fourt et al. |
| 10,118,001 B2 | 11/2018 | Fourt et al. |
| 10,314,981 B2 | 6/2019 | Sampson et al. |
| 10,350,362 B2 | 7/2019 | Dennis, Jr. et al. |
| 10,363,377 B2 | 7/2019 | Atterbury et al. |
| 11,298,462 B2 | 4/2022 | Atterbury et al. |
| 11,331,432 B2 | 5/2022 | Holmqvist et al. |
| 11,369,751 B2 | 6/2022 | Ruan et al. |
| 11,452,821 B2 | 9/2022 | LaFever et al. |
| 2002/0055712 A1 | 5/2002 | Neracher |
| 2004/0039336 A1 | 2/2004 | Amark et al. |
| 2005/0101919 A1 | 5/2005 | Brunnberg |
| 2005/0273061 A1 | 12/2005 | Hommann et al. |
| 2006/0224124 A1 | 10/2006 | Scherer |
| 2007/0270777 A1 | 11/2007 | Dacquay et al. |
| 2008/0097311 A1 | 4/2008 | Dacquay et al. |
| 2008/0097390 A1 | 4/2008 | Dacquay et al. |
| 2008/0269692 A1 | 10/2008 | James et al. |
| 2009/0036868 A1 | 2/2009 | Pinedjian et al. |
| 2009/0281496 A1* | 11/2009 | Matusch ............ A61M 5/31501 604/134 |
| 2010/0211005 A1 | 8/2010 | Edwards et al. |
| 2011/0054414 A1* | 3/2011 | Shang ............... A61M 5/31578 604/218 |
| 2011/0144594 A1* | 6/2011 | Sund ................. A61M 5/31571 604/228 |
| 2011/0202011 A1 | 8/2011 | Wozencroft |
| 2011/0319813 A1 | 12/2011 | Kamen et al. |
| 2013/0237921 A1 | 9/2013 | Lannan et al. |
| 2013/0267897 A1 | 10/2013 | Kemp et al. |
| 2014/0236076 A1 | 8/2014 | Marshall et al. |
| 2014/0249483 A1 | 9/2014 | Kiilerich et al. |
| 2014/0263156 A1 | 9/2014 | Newsom et al. |
| 2014/0276637 A1 | 9/2014 | Massey, Jr. |
| 2015/0246180 A1 | 9/2015 | Fenlon et al. |
| 2015/0273162 A1 | 10/2015 | Holmqvist |
| 2016/0001015 A1 | 1/2016 | Kucuk et al. |
| 2016/0354555 A1 | 12/2016 | Gibson et al. |
| 2016/0367763 A1 | 12/2016 | Tschirren et al. |
| 2017/0215699 A1 | 8/2017 | Ouyang et al. |
| 2017/0216526 A1 | 8/2017 | Brereton et al. |
| 2017/0224929 A1 | 8/2017 | Sampson et al. |
| 2017/0246403 A1 | 8/2017 | Cowe et al. |
| 2017/0361034 A1 | 12/2017 | Scheller et al. |
| 2018/0250471 A1 | 9/2018 | Grimoldby et al. |
| 2018/0339114 A1 | 11/2018 | Wendland et al. |
| 2019/0030249 A1 | 1/2019 | Gonzalez et al. |
| 2019/0192785 A1 | 6/2019 | Wendland et al. |
| 2019/0366000 A1 | 12/2019 | Cowe et al. |
| 2020/0114041 A1 | 4/2020 | Alas et al. |
| 2020/0316314 A1 | 10/2020 | Buri et al. |
| 2021/0077732 A1 | 3/2021 | Egelhofer |
| 2021/0196900 A1 | 7/2021 | Apply et al. |
| 2022/0015429 A1 | 1/2022 | Brown et al. |
| 2022/0176042 A1 | 6/2022 | Belisle |
| 2022/0395640 A1 | 12/2022 | Schwartzentruber |
| 2023/0001099 A1 | 1/2023 | Dunn |
| 2023/0238105 A1 | 7/2023 | Schneider et al. |
| 2023/0347074 A1 | 11/2023 | Gavin |
| 2024/0009397 A1 | 1/2024 | In et al. |

FOREIGN PATENT DOCUMENTS

| | | |
|---|---|---|
| WO | WO 2002/047746 A1 | 6/2002 |
| WO | WO 2011/109205 A2 | 9/2011 |
| WO | WO 2016/081238 A1 | 5/2016 |
| WO | WO 2019/074788 A1 | 4/2019 |
| WO | WO 2020/190529 A1 | 9/2020 |

OTHER PUBLICATIONS

U.S. Appl. No. 18/640,163, filed Apr. 19, 2024, Alexander Hee-Hanson.
U.S. Appl. No. 18/640,292, filed Apr. 19, 2024, Alexander Hee-Hanson.
U.S. Appl. No. 18/640,427, filed Apr. 19, 2024, Alexander Hee-Hanson.
U.S. Appl. No. 18/640,710, filed Apr. 19, 2024, Alexander Hee-Hanson.

* cited by examiner

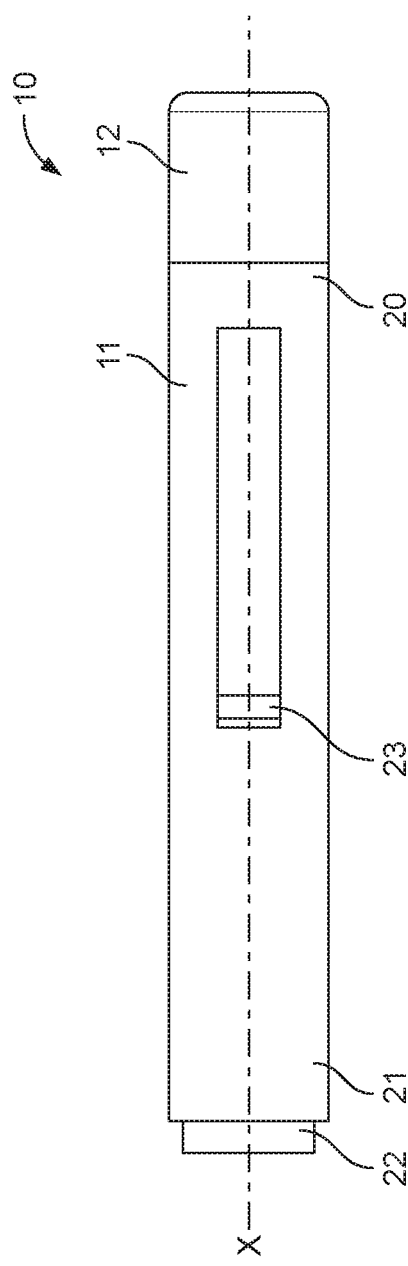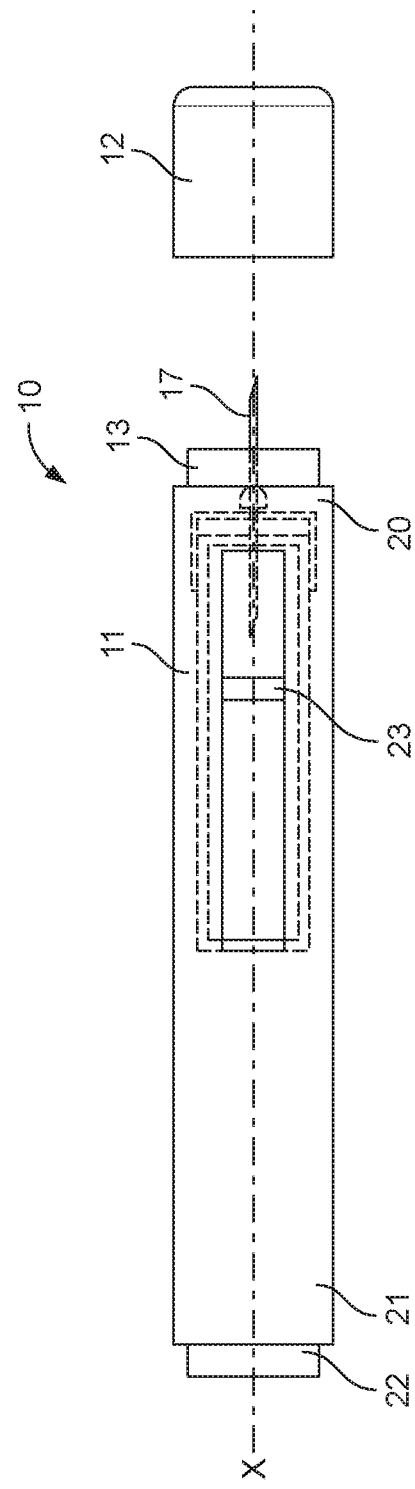
FIG. 1A
FIG. 1B

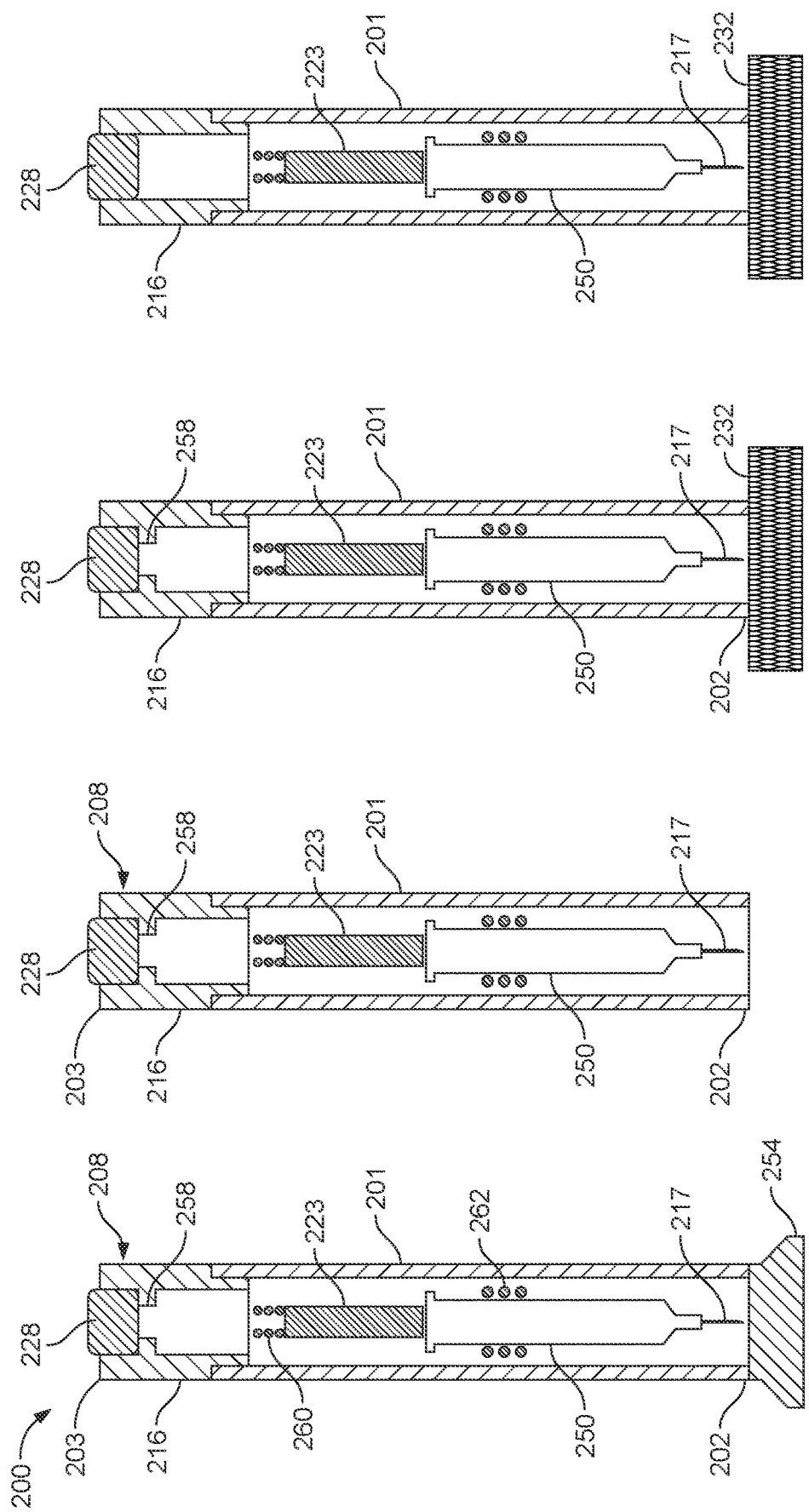

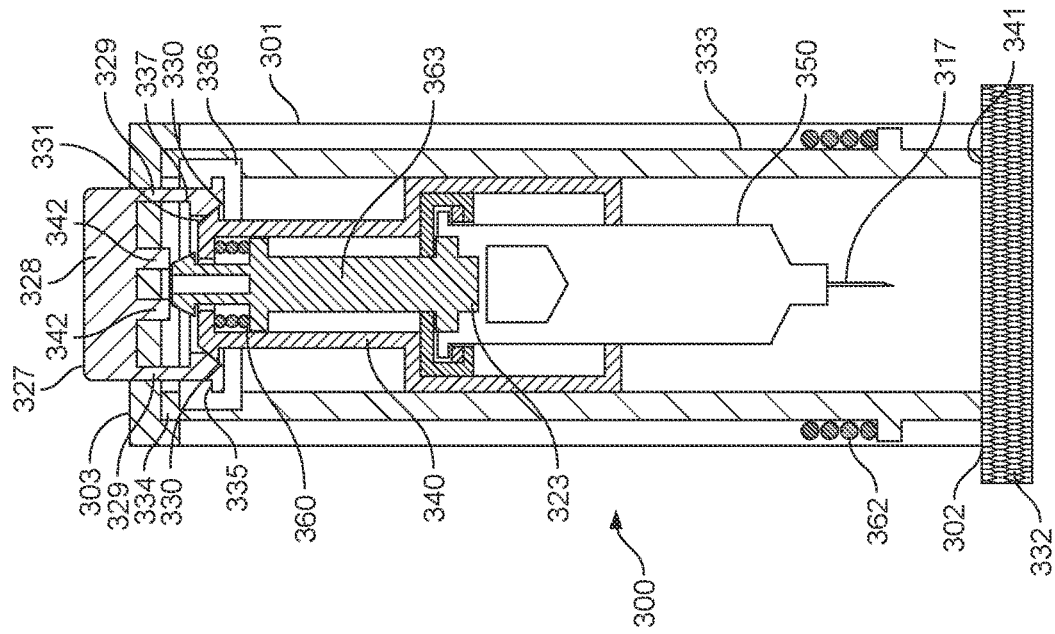
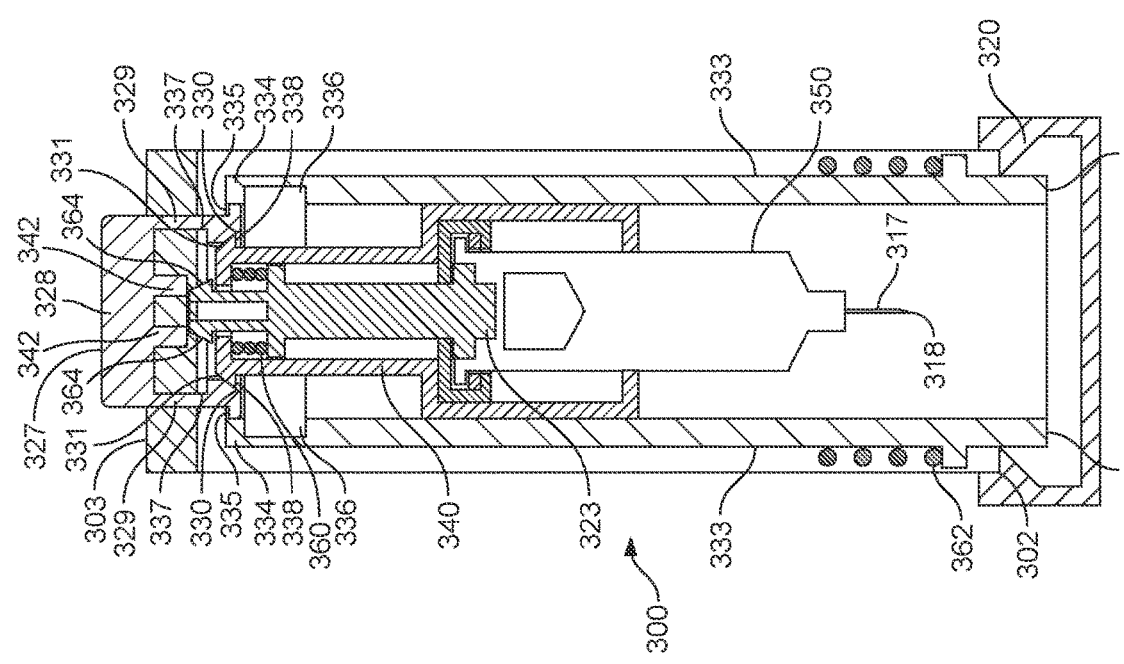

MEDICAMENT DELIVERY DEVICE

TECHNICAL FIELD

The present disclosure relates to a medicament delivery device and to a method of using a medicament delivery device.

BACKGROUND

Medicament delivery devices, such as auto-injectors, dispense medicament to an injection site of a patient. In some cases, a needle actuator is able to be depressed irrespective of whether the device has been placed at an injection site. Depressing the needle actuator independently of the device being placed at an injection site can cause the needle to be unintentionally exposed for stick injuries and can cause a dose of medicament to be unintentionally dispensed. This can also lead to a waste of medicament.

SUMMARY

According to a first aspect, a medicament delivery device includes a body having a proximal end and a distal end, a needle for injecting medicament into a user, the needle is movable relative to the body from a pre-use position to an injecting position, in the pre-use position the distal end of the needle is located within the body, and in the injecting position the distal end of the needle protrudes outside of the distal end of the body for injecting medicament into the user, an actuation member which is movable relative to the body from a first position to a second position for causing the needle to move from the pre-use position to the injecting position, the second position is located distally from the first position, the actuation member comprises a flexible arm comprising an engagement surface, the device further comprises a contoured surface, when the actuation member is in the first position the engagement surface engages the contoured surface, and when the actuation member moves distally from the first position to the second position, the flexible arm is deflected radially by the engagement of the engagement surface with the contoured surface, and a blocking member for blocking movement of the actuation member from the first position to the second position, the blocking member is movable relative to the body between an extended position and a retracted position, in the extended position, the distal end of the blocking member protrudes distally from the distal end of the body, and the retracted position is located proximally from the extended position, the blocking member comprises a proximal portion which engages the flexible arm when the blocking member is in the extended position and the actuation member is in the first position for preventing distal movement of the flexible arm by preventing the flexible arm from being deflected radially by the contoured surface, and when the blocking member is in the retracted position, the proximal portion is disengaged from the flexible arm for permitting the flexible arm to be deflected radially by the contoured surface as the flexible arm moves distally.

In some embodiments, the flexible arm comprises a radially-extending protrusion which engages the proximal portion of the blocking member when the blocking member is in the extended position and the actuation member is in the first position.

In some embodiments, the blocking member comprises an axially-extending recess located distally from the proximal portion for at least partially receiving the radially-extending protrusion when the flexible arm is deflected radially by the contoured surface.

In some embodiments, the flexible arm comprises an axially-extending recess located proximal of the engagement surface for at least partially receiving the contoured surface to allow the flexible arm to move radially towards an unflexed position when the engagement surface moves distally past the contoured surface.

In some embodiments, the device further comprises a locking surface, and the axially extending recess of the flexible arm comprises an abutment surface which is configured to engage the locking surface for preventing proximal movement of the actuation member from the second position to the first position.

In some embodiments, the contoured surface is fixed relative to the body and/or located within the body.

In some embodiments, the device further comprises an inner body located within the body. In some cases, the contoured surface is provided on the inner body.

In some embodiments, the locking surface is provided on the inner body.

In some embodiments, the proximal portion of the blocking member is located radially outwardly of the radially-extending protrusion when the blocking member is in the extended position and the actuation member is in the first position.

In some embodiments, the proximal portion of the blocking member is located radially inwardly of the radially-extending protrusion when the blocking member is in the extended position and the actuation member is in the first position.

In some embodiments, the device further comprises a biasing means for biasing the blocking member in a direction from the retracted position towards the extended position. In some cases, the biasing means comprises a spring.

In some embodiments, the device further comprises a cap which is removably attachable to the body, the cap covers the distal end of the blocking member for preventing the blocking member being moved from the extended position to the retracted position when the cap is attached to the body.

In some embodiments, the contoured surface comprises a planar surface and/or the engagement surface comprises a planar surface.

In some embodiments, the contoured surface comprises a curved surface and/or the engagement surface comprises a curved surface.

In some embodiments, the device further comprises a lock ring which is rotatable from a pre-use position, in which the lock ring prevents movement of the actuation member from the first position towards the second position, to a use position in which the lock ring permits movement of the actuation member from the first position towards the second position.

In some embodiments, the blocking member comprises a radially-extending protrusion comprising a contoured surface configured to engage the flexible arm and radially deflect the flexible arm when the actuation member moves from the first position towards the second position.

In some embodiments, the radially-extending protrusion on the blocking member comprises a locking surface configured to engage a radially-extending protrusion on the flexible arm to hold the blocking member in the retracted position when the actuation member is in the second position.

In some embodiments, the device comprises a mechanism for automatically moving the needle from the pre-use position to the injecting position.

In some embodiments, the mechanism is activated by moving the actuation member from the first position to the second position.

In some embodiments, the mechanism is configured to not be activated by moving the blocking member from the extended position to the retracted position.

In some embodiments, the blocking member comprise a sleeve.

In some embodiments, the actuation member comprise a button for pressing by a user for moving the actuation member from the first position to the second position. In some cases, the button at least partially protrudes from the body when the actuation member is in the first position. In some cases, the button at least partially protrudes from the proximal end of the body when the actuation member is in the first position.

In some embodiments, the actuation member is in the form of a button.

In some embodiments, the device further comprises a container containing the medicament. In some examples, the container comprises a syringe. In some examples, the syringe comprises the needle. In some examples, the medicament is contained in the syringe. In some examples, the medicament is not contained in the syringe.

According to an aspect, a method of using a medicament delivery device includes moving a distal end of a blocking member proximally relative to a body from an extended position to a retracted position, in the extended position, the distal end of the blocking member protrudes distally from the distal end of the body, and when the blocking member is in the extended position, the blocking member is configured to prevent movement of an actuation member from a first position to a second position, and when the blocking member is in the retracted position, the blocking member is configured to permit movement of the actuation member from the first position to the second position for causing a needle to move from a pre-use position in which the distal end of the needle is located within the body to an injecting position in which the distal end of the needle protrudes outside of the distal end of the body for injecting medicament into a user.

In some embodiments, the method comprises using a medicament delivery device having any of the features described herein.

According to an aspect, a method of using a medicament delivery device includes pressing a distal end of a blocking member against an injection site to move the blocking member relative to a body from an extended position to a retracted position, and moving an actuation member from a first position to a second position to activate a mechanism which automatically moves a needle from a pre-use position, in which the distal end of the needle is located within the body, to an injecting position in which the distal end of the needle protrudes outside of the distal end of the body for injecting medicament.

In some embodiments, the method further comprises rotating a lock ring from a pre-use position, in which the lock ring prevents movement of the actuation member from the first position towards the second position, to a use position in which the lock ring permits movement of the actuation member from the first position towards the second position.

In some embodiments, the method further comprises rotating the lock ring prior to pressing the distal end of the blocking member against the injection site.

In some embodiments, the method further comprises removing a cap from the medicament delivery device.

According to an aspect, a medicament delivery device includes:
  a body having a proximal end and a distal end;
  a needle configured to be movable relative to the body from (i) an initial position in which a distal end of the needle is proximal to the distal end the body, to (ii) an injection position in which the distal end of the needle is distal to the distal end of the body for injecting a medicament,
  an actuation member configured to be distally movable relative to the body from (i) a first position to (ii) a second position, the medicament delivery device being configured such that moving the actuation member relative to the body from the first position to the second position causes the needle to move from the initial position to the injection position, the actuation member comprising a flexible arm comprising an engagement surface;
  a contoured surface configured to engage the engagement surface when the actuation member is in the first position, the medicament delivery device being configured such that when the actuation member moves distally from the first position to the second position, the flexible arm is deflected radially by the engagement of the engagement surface and the contoured surface; and
  a blocking member configured to limit movement of the actuation member from the first position to the second position, the blocking member being movable relative to the body between (i) an extended position in which a distal end of the blocking member is distal to the distal end of the body and (ii) a retracted position located proximally from the extended position,
  wherein the blocking member comprises a proximal portion configured to engage the flexible arm when the blocking member is in the extended position and the actuation member is in the first position to limit distal movement of the flexible arm relative to the body by limiting the flexible arm from being deflected radially by the contoured surface, and
  wherein the medicament delivery device is configured such that when the blocking member is in the retracted position, the proximal portion is disengaged from the flexible arm to allow the flexible arm to be deflected radially by the contoured surface as the flexible arm moves distally relative to the body.

In some embodiments, the flexible arm comprises a radially-extending protrusion configured to engage the proximal portion of the blocking member when the blocking member is in the extended position and the actuation member is in the first position.

In some embodiments, the blocking member comprises an axially-extending recess located distally from the proximal portion for at least partially receiving the radially-extending protrusion when the flexible arm is deflected radially by the contoured surface.

In some embodiments, the proximal portion of the blocking member is located radially outwardly of the radially-extending protrusion when the blocking member is in the extended position and the actuation member is in the first position.

In some embodiments, the proximal portion of the blocking member is located radially inwardly of the radially-extending protrusion when the blocking member is in the extended position and the actuation member is in the first position.

In some embodiments, the flexible arm comprises an axially-extending recess located proximal of the engagement surface for at least partially receiving the contoured surface to allow the flexible arm to move radially towards an unflexed position when the engagement surface moves distally beyond the contoured surface.

In some embodiments, the medicament delivery device includes a locking surface, and the axially extending recess of the flexible arm comprises an abutment surface configured to engage the locking surface for limiting proximal movement of the actuation member from the second position to the first position.

In some embodiments, the contoured surface is fixed relative to the body or is located within the body. In some cases, the contoured surface is fixed relative to the body and located within the body.

In some embodiments, medicament delivery device includes an inner body located within the body, the inner body comprising the contoured surface.

In some embodiments, the medicament delivery device includes a biasing member for biasing the blocking member in a direction from the retracted position towards the extended position. In some cases, the biasing member comprises or is a spring.

In some embodiments, medicament delivery device includes a cap removably attachable to the body, the cap configured to cover the distal end of the blocking member to limit the blocking member from being moved from the extended position to the retracted position when the cap is attached to the body.

In some embodiments, at least one of the contoured surface or the engagement surface comprises a planar surface. In some cases, the contoured surface and the engagement surface comprises respective planar surfaces.

In some embodiments, at least one of the contoured surface or the engagement surface comprises a curved surface. In some cases, the contoured surface and the engagement surface comprise respective curved surfaces.

In some embodiments, the medicament delivery device includes a lock ring configured to rotate from (i) a first lock ring position in which the lock ring limits movement of the actuation member from the first position towards the second position to (ii) a second lock ring position in which the lock ring allows movement of the actuation member from the first position towards the second position.

In some embodiments, the blocking member comprises a radially-extending protrusion comprising a contoured surface configured to engage the flexible arm and radially deflect the flexible arm when the actuation member moves from the first position towards the second position.

In some embodiments, the radially-extending protrusion on the blocking member comprises a locking surface configured to engage a radially-extending protrusion on the flexible arm and to hold the blocking member in the retracted position when the actuation member is in the second position.

In some embodiments, the actuation member comprises a button configured to be pressed by a user to move the actuation member from the first position to the second position, wherein at least a portion of the button protrudes from the body when the actuation member is in the first position.

In some embodiments, a proximal end of the button is proximal to the proximal end of the body when the actuation member is in the first position.

In some embodiments, the medicament delivery device includes a container containing the medicament. In some cases, the container comprises a syringe, and the syringe comprises the needle.

In some embodiments, the medicament delivery device includes a mechanism for automatically (e.g., without further user assistance) moving the needle from the initial position to the injection position.

In some embodiments, the mechanism is configured to be activated by moving the actuation member from the first position to the second position.

In some embodiments, the mechanism is configured such that moving the blocking member from the extended position to the retracted position does not activate the mechanism.

In some embodiments, wherein the blocking member comprises a sleeve.

In an aspect, a medicament delivery device includes:
a body;
a first member configured to be axially movable relative to the body, the first member comprising a first resilient arm;
a second member configured to be axially movable relative to the body, the second member comprising a second resilient arm;
a third member configured to be axially movable relative to the body, the third member configured to releasably engage the first resilient arm of the first member to releasably limit a movement of the resilient arm relative to the third member and releasably limit a distal movement of the first member relative to the body; and
a fourth member configured to releasably engage the first resilient arm of the first member to cause the first resilient arm to move into a recess of the third member and to allow the distal movement of the first member relative to the body,
wherein the medicament delivery device is configured such that the distal movement of the first member relative to the body flexes the second resilient arm and causes a medicament to be dispensed from the medicament delivery device.

In an aspect, a method includes moving a distal end of a blocking member of a medicament delivery device proximally relative to a body of the medicament delivery device from (i) an extended in which (a) a distal end of the blocking member is distal to a distal end of the body and (b) the blocking member limits movement of an actuation member of the medicament delivery device from a first position to a second position to (ii) a retracted position in which the blocking member allows movement of the actuation member from the first position to the second position for causing a needle to move from an initial position in which a distal end of the needle is located proximal to a proximal end of the body to an injection position in which the distal end of the needle is distal to the distal end of the body for injecting medicament into a user.

In an aspect, a method includes:
pressing a distal end of a blocking member of a medicament delivery device against an injection site to move the blocking member relative to a body of the medicament delivery device from an extended position to a retracted position, and
moving an actuation member of the medicament delivery device from a first position to a second position to activate a mechanism that automatically moves a needle from (i) an initial position in which a distal end of the needle is proximal to a distal end of the body to (ii) an injection position in which the distal end of the needle is distal to the distal end of the body for injecting medicament.

In some embodiments, the method includes rotating a lock ring from (i) a first lock ring position in which the lock ring limits movement of the actuation member from the first position towards the second position to (ii) a second lock ring position in which the lock ring allows movement of the actuation member from the first position towards the second position.

In some embodiments, the method includes rotating the lock ring prior to pressing the distal end of the blocking member against the injection site.

In some embodiments, the method includes removing a cap from the medicament delivery device.

BRIEF DESCRIPTION OF THE DRAWINGS

Embodiments will now be described, by way of example only, with reference to the accompanying drawings, in which:

FIG. 1A is a schematic view of a medicament delivery device with a cap attached;

FIG. 1B is a schematic view of the medicament delivery device of FIG. 1A with the cap removed;

FIG. 2A is a schematic view of a medicament delivery device prior to use (i.e. in a pre-use configuration);

FIG. 2B is a schematic view of the device of FIG. 2A with the cap removed;

FIG. 2C is a schematic view of the device of FIG. 2A showing the device placed at an injection site;

FIG. 2D is a schematic view of the device of FIG. 2A with a lock ring of the device having been rotated to allow a button of the device to be depressed by a user;

FIG. 3A is a schematic view of parts of a medicament delivery device;

FIG. 3B is a schematic view of the device of FIG. 3A with the cap removed and the device pressed against an injection site, with the blocking member in the retracted position;

DETAILED DESCRIPTION

Figure 2G:
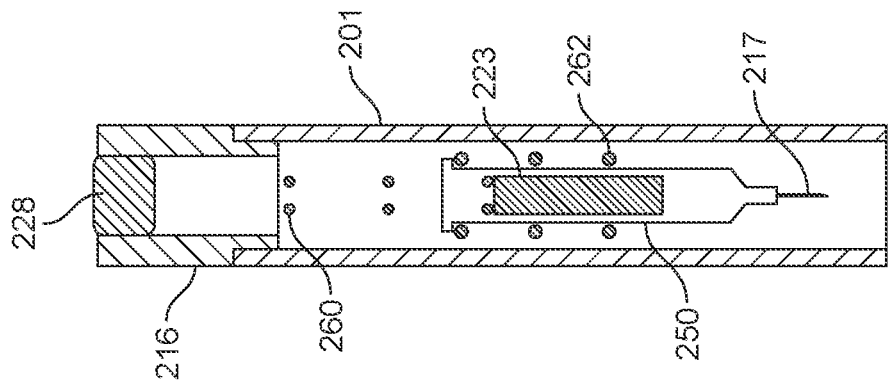
FIG. 2G is a schematic view of the device of FIG. 2A showing the device removed from the injection site after the needle has retracted within the device after delivery of the dose.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically a user must remove cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 1A & 1B, button 22 is located at a proximal end of housing 11. However, in other embodiments, button 22 could be located on a side of housing 11.

Other manual or automated features can include drug injection or needle retraction, or both. Injection is the process by which a bung or piston 23 is moved from a proximal location within a syringe to a more distal location within the syringe in order to force a medicament from the syringe through needle 17. In some embodiments, a drive spring is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17.

Following injection, needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11.

Another form of needle retraction can occur if needle 17 is moved relative to housing 11. Such movement can occur if the syringe within housing 11 is moved in a proximal direction relative to housing 11. This proximal movement can be achieved by using a retraction spring, located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

FIGS. 2A to 2G show the sequential steps of operating a medicament injection device 400.

As shown in FIG. 2A, the device 200 comprises a body 201, a syringe having a needle 217 and an axially movable plunger 223 for dispensing medicament from the syringe 250. The device comprises a cap 254 which is removably attached to the body 201 and covers a distal end 202 of the body 201 so as to prevent stick injuries.

As shown in FIGS. 2B-2C, in order to deliver a dose of medicament to an injection site, the cap 254 is removed (FIG. 2B) and the device is placed at an injection site 232 (FIG. 2C). A needle actuator in the form of a button 228, is prevented from being depressed by a locking member 208 in the form of a lock ring 216 which is rotatable by a user about a longitudinal axis of the device, by a radially projecting stop 258 provided in the locking member 208. In FIG. 2D, in order to allow the button 228 to be depressed by a user, the lock ring 216 is rotated about the longitudinal axis of the device to a needle actuator release position (or button release position) in which the stop 258 no longer prevents the button 228 from being depressed by a user.

Figure 2F:
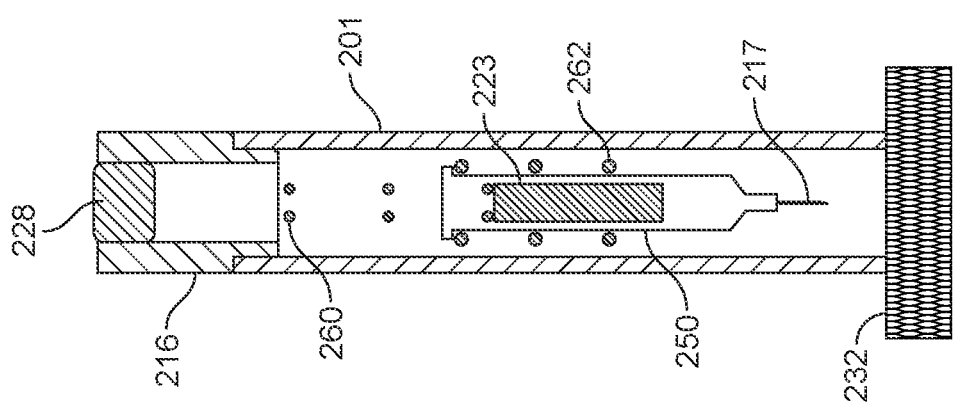
FIG. 2F is a schematic view of the device of FIG. 2A showing the needle retracted within the device after a dose has been delivered.
Figure 2E:
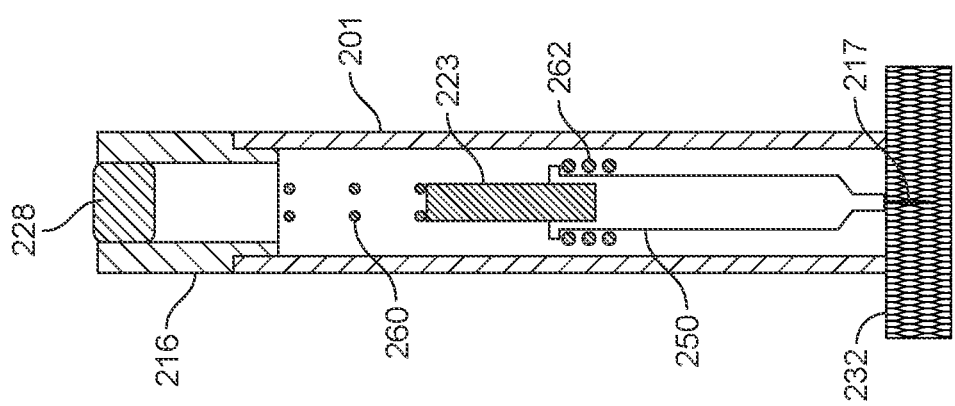
FIG. 2E is a schematic view of the device of FIG. 2A after the button has been depressed and the needle has been caused to move to an exposed position.

Turning now to FIG. 2E, the user then depresses the button 228 to actuate or trigger a needle mechanism so as to release the syringe 250 for distal axial movement towards the injection site 232 such that the needle 217 moves from a pre-use retracted position to an exposed (or "uncovered") position for delivering medicament to the injection site 232 under a biasing force provided by a bias in the form of a compression spring 260. Depressing the button 228 also releases the plunger 223 which, biased by the bias 260, moves along the syringe 250 towards the distal end 204 of the device 200 to force medicament within the syringe 250 through the needle 217, thereby delivering a dose of medicament. As shown in FIG. 2F, once the dose has been delivered, a medicament container bias 262, embodied by a further spring 262, then causes the needle 202 to move axially back to the retracted position, away from the injection site 232 in a proximal direction. As shown in FIG. 2G, the device 200 is then removed from the injection site 232, for later reuse or for disposal.

FIG. 3A is a schematic view of parts of a medicament delivery device 300.

Figure 3D:
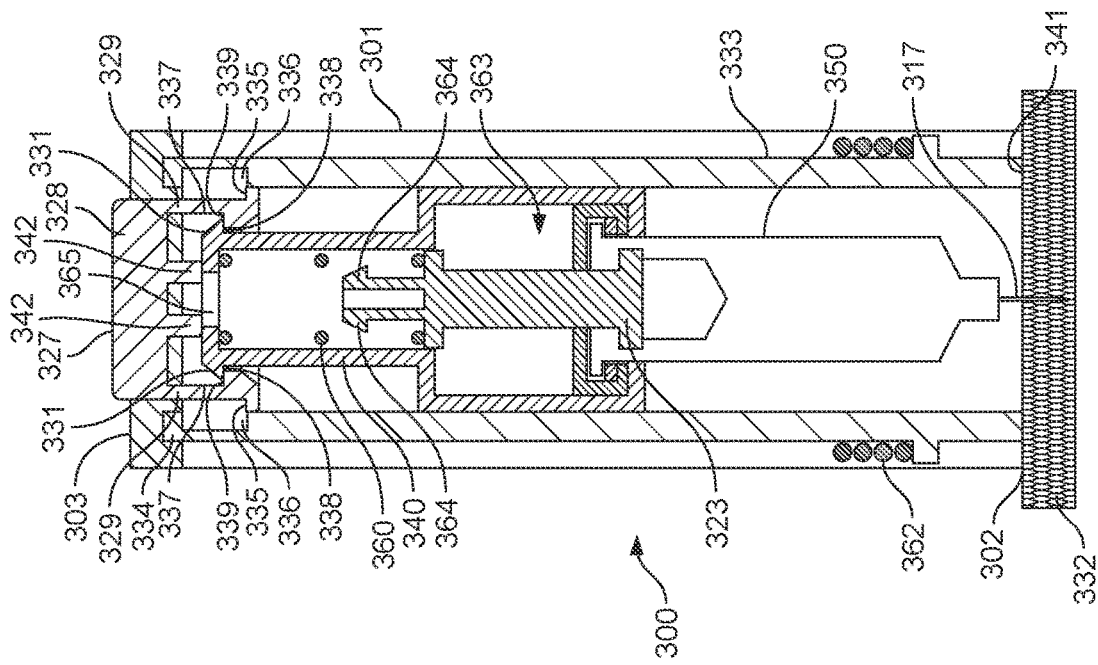
FIG. 3D is a schematic view of the device of FIG. 3A with the actuation member in the second position.

The medicament delivery device 300 comprises a body 301 having a proximal end 303 and a distal end 302. The device 300 has a needle 317 for injecting medicament into a user. The needle 317 is movable relative to the body 301 from a pre-use position to an injecting position. In the pre-use position the distal end of the needle 318 is located within the body 301, and in the injecting position the distal end of the needle 318 protrudes outside of the distal end of the body 301 for injecting medicament into the user. FIG. 3A shows an example of the needle 317 in the pre-use position, and FIG. 3D shows an example of the needle 317 in the injecting position.

The needle 317 is part of a syringe 350 which contains medicament. In some embodiments, a container such as a cartridge of medicament is included which is initially separated from the needle.

The medicament delivery device 300 comprises an actuation member 327. The actuation member 327 is movable relative to the body 301 from a first position to a second position for moving the needle 317 from the pre-use position to the injecting position. FIG. 3A shows an example of the actuation member 327 in the first position. FIG. 3D shows an example of the actuation member 327 in the second position. The second position is located distally from the first position.

The actuation member has a flexible arm 329 comprising an engagement surface 330. The device 300 further comprises a contoured surface 331. When the actuation member 327 is in the first position the engagement surface 330 engages the contoured surface 331. When the actuation member 327 moves from the first position to the second position, the flexible arm 329 is deflected radially by the engagement of the engagement surface 330 with the contoured surface 331 as the flexible arm 329 moves distally.

The contoured surface 331 is a planar surface. The engagement surface 330 is a planar surface. In some embodiments, the contoured surface 331 may have a curved surface instead of or in addition to a planar surface. In some embodiments, the engagement surface 330 may have a curved surface instead of or in addition to a planar surface.

The actuation member 327 has a button 328 for pressing by a user. The button 328 protrudes from the proximal end of the body 301 when the actuation member 327 is in the first position. In some embodiments, the button 328 can protrude from a side of the body, for example. Pressing the button 328 moves the actuation member 327 from the first position to the second position.

The device 300 has a blocking member 333 for blocking movement of the actuation member 327 from the first position to the second position. The blocking member 333 is located within the body 301. The blocking member 333 is movable relative to the body 301 between an extended position and a retracted position. In the extended position, the distal end 341 of the blocking member 333 protrudes distally from the distal end 302 of the body 301, as shown, for example in FIG. 3A. FIG. 3B shows an example of the blocking member 333 in the retracted position, in which the distal end 341 of the blocking member 333 is flush with the distal end of the body 302. The blocking member 333 is in the retracted position in FIGS. 3C and 3D. In some embodiments, the distal end 341 of the blocking member 333 may be located distally from the distal end 302 of the body when the blocking member is in the retracted position. The retracted position is located proximally from the extended position.

The medicament delivery device 300 has a biasing means in the form of a spring 362 for biasing the blocking member 333 towards the extended position. The spring 362 allows the blocking member 333 to return to the extended position if the blocking member 333 is removed from the injection site. In some embodiments, the spring 362 may be omitted, for example to reduce the cost or mass of the device, or the force required to move the blocking member proximally.

The blocking member 333 comprises a proximal portion 334 which engages a radially extending protrusion 335 on the flexible arm 329 when the blocking member 333 is in the extended position and the actuation member is in the first position as shown, for example, in FIG. 3A. The engagement of the proximal portion 334 with the radially-extending protrusion 335 prevents the flexible arm 329 from being deflected radially by the contoured surface 331. When the blocking member 333 is in the retracted position, the proximal portion 334 is disengaged from the radially extending protrusion 335 for permitting the flexible arm 329 to be deflected radially by the contoured surface 331 as the flexible arm 329 moves distally. In some embodiments, the flexible arm 329 does not comprise a radially extending protrusion.

Figure 3C:
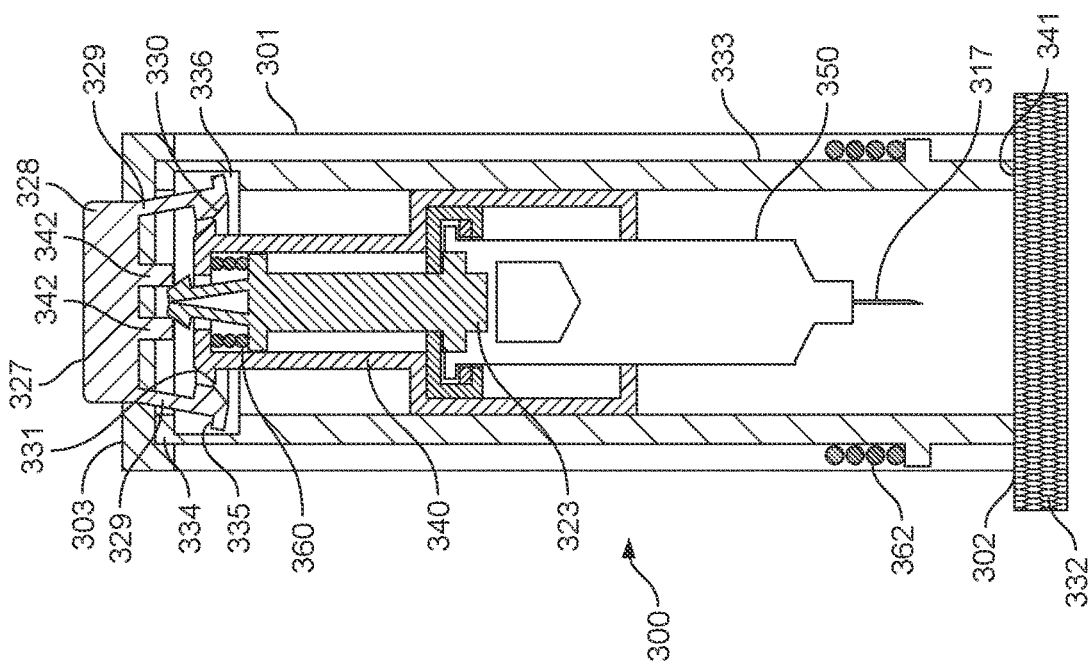
FIG. 3C is a schematic view of the device of FIG. 3A with the actuation member positioned between a first position and a second position.

The blocking member 333 comprises an axially-extending recess 336 located distally from the proximal portion 334 for at least partially receiving the radially-extending protrusion 335 when the flexible arm 329 is deflected radially by the contoured surface as shown, for example, in FIG. 3C.

The flexible arm 329 comprises an axially-extending recess 337 located proximal of the engagement surface 330 for at least partially receiving the contoured surface 331 as shown, for example, in FIG. 3D. This allows the flexible arm 329 to move radially towards an unflexed position when the engagement surface 330 moves distally past the contoured surface.

The device 300 further comprises a locking surface 338. The axially extending recess 337 of the flexible arm 329 comprises an abutment surface 339 which engages the locking surface 338 for preventing proximal movement of the actuation member 327 from the second position to the first position as shown, for example, in FIG. 3D. The locked position of the actuation member 327 indicates to a user that the device has been operated. In some embodiments, there is no locking surface 338 and the action member 327 is free to return to the first position after it has been moved to the second position.

In some embodiments, the contoured surface 331 is fixed relative to the body 301. The contoured surface 331 is located within the body 301. The contoured surface 331 and the locking surface 338 are both provided on a protrusion. In the example shown in FIGS. 3A to 3D, the contoured surface is provided on an inner body 340 located within the body 301. The locking surface 338 is also provided on the inner body 340. In some embodiments, the contoured surface 331 and/or the locking surface 338 can be provided on the body itself.

In the embodiment of FIGS. 3A to 3D, the proximal portion 334 of the blocking member 333 is located radially outwardly of the radially-extending protrusion 335 when the blocking member 333 is in the extended position and the actuation member 327 is in the first position. The flexible arm 329 is deflected radially outwardly by the engagement of the engagement surface 330 and the contoured surface 331 as the flexible arm 329 moves distally.

Although one flexible arm 327 and contoured surface 331 have been described, the device 300 of FIGS. 3A to 3D has two flexible arms 327 which each co-operate with a separate contoured surface 331. It will be appreciated that one flexible arm 327 and contoured surface 331 or more than two flexible arms 327 and contoured surfaces 331 can be provided in some embodiments.

The blocking member 333 comprises a sleeve. The sleeve is located within the body 301. In some embodiments, the blocking member 333 could comprise an axially-extending member which is not in the form of the sleeve. The sleeve is co-axial or substantially co-axial with the longitudinal axis of the body. The sleeve may be rotationally-fixed relative to the body.

The actuation member 327 is movable relative to the body from a first position to a second position for causing the needle to move from the pre-use position to the injecting position. When the actuation member 327 is in the second position, the needle 317 is moved to its injecting position. This can be by the actuation member 327 exerting a force which moves the needle 317 directly or the actuation member 327 can activate a mechanism which automatically causes the needle 317 to move to the injecting position when the actuation member 327 is in the second position.

The example device 300 comprises a mechanism 363 for automatically moving the needle from the pre-use position to the injecting position. The mechanism 363 comprises a plunger 323 and a spring 360. The plunger 323 is biased distally by the spring 360. The mechanism 363 is at least partially housed within an inner body 340. The plunger 323 comprises proximally-extending clips 364. The spring 360 is retained in the compressed position by virtue of the clips 364 which protrude through a proximal opening 365 in the inner body 340. The clips 365 engage with the inner body 340 for maintaining the plunger 323 in a proximal position.

The mechanism 363 is activated by the user moving the actuation member 327 from the first position to the second position. When the actuation member 327 is in the second position, the spring 360 is released to move the plunger distally to thereby move the syringe 350 distally, and to dispense the medicament from the syringe 350 via the needle 317 as the plunger 323 moves distally within the syringe 350. The actuation member 327 has one or more protrusions 342 which engage with the clips 364 to flex the clips radially inwardly for allowing the clips to move distally through the proximal opening 365, thereby releasing the spring 360.

Some embodiments use a different mechanism. In some embodiments, movement of the actuation member 327 from the first position to the second position causes (e.g., only causes) the needle 317 to move from the pre-use position to the injecting position. In some embodiments, movement of the actuation member 327 from the first position to the second position causes additional steps to be performed, such as the automatic dispensing of the medicament from the device via the needle.

In some embodiments, the movement of the blocking member 333 from the extended position to the retracted position does not activate the mechanism 363 for automatically moving the needle from the pre-use position to the injecting position.

The medicament delivery device 300 may additionally comprise a lock ring 216, as shown and described in relation to FIGS. 2A to 2G above. The lock ring is rotatable from a pre-use position, in which the lock ring prevents movement of the actuation member from the first position towards the second position, to a use position in which the lock ring permits movement of the actuation member from the first position towards the second position.

The medicament delivery device 300 additionally has a cap 320. The cap 320 is removably attached to the body 301 and covers the distal end of the blocking member 341 for preventing the blocking member 300 from being moved from the extended position to the retracted position when the cap 320 is attached to the body 301. The cap 320 prevents the device being accidentally activated prior to the cap 320 being removed from the body 301 since the actuation member 327 cannot be moved from the first position to the second position when the blocking member 333 is in the extended position. The cap 320 may be attached to the body 301, for example, by a screw-threaded or a press fit connection. The cap 320 is optional and in some embodiments the device may not have a cap.

In use, a user removes the cap 320. A user then places the distal end 341 of the blocking member 333 against an injection site to move the blocking member 333 from the extended position to the retracted position as shown, for example, in FIG. 3B.

A user then presses the button 328 into the body 301. The flexible arm 329 is deflected radially by the engagement of the engagement surface 330 with the contoured surface 331 as the flexible arm 329 moves distally as shown, for example, in FIG. 3C.

The radially-extending protrusion 335 is at least partially received in the axially-extending recess 336 of the blocking member 333 when the flexible arm 329 is deflected radially by the contoured surface, and as the flexible arm 329 moves distally towards the second position.

When the engagement surface 330 moves distally past the contoured surface, the contoured surface 331 is at least partially received in the axially-extending recess 337 of the flexible arm 329 to allow the flexible arm 329 to move radially towards an unflexed position as shown, for example, in FIG. 3D.

The axially-extending recess 337 of the flexible arm 329 comprises an abutment surface 339 which engages the locking surface 338 for preventing proximal movement of the actuation member 327 from the second position to the first position as shown, for example, in FIG. 3D.

In the medicament delivery device 300, the proximal portion 334 of the blocking member 333 is located radially-outwardly of the radially-extending protrusion 335 when the blocking member is in the extended position and the actuation member is in the first position. The flexible arm 329 is deflected radially outwards by the engagement of the engagement surface 330 with the contoured surface 331 as the flexible arm 329 moves distally.

Figure 4:
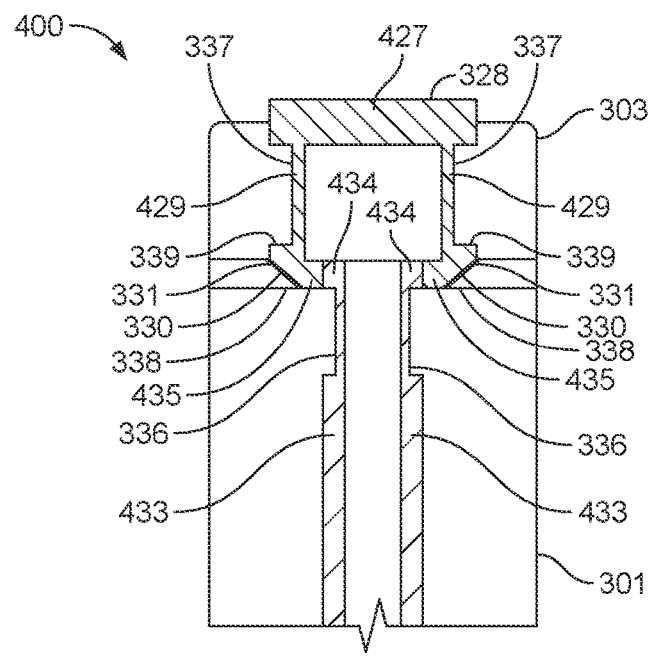
FIG. 4 is a schematic view of parts of a medicament delivery device.

FIG. 4 is a view of part of a medicament delivery device 400. The medicament delivery device 400 is similar to the medicament delivery device 300 described above, and has corresponding reference numerals for corresponding features. A difference of the embodiment of FIG. 4 compared to the medicament delivery device 300 is that the proximal portion 434 of the blocking member 433 is located radially inwardly of the radially-extending protrusion 435 of the flexible arm 429 when the blocking member 433 is in the extended position and the actuation member 427 is in the first position. The flexible arm 429 is deflected radially inwardly by the engagement of the engagement surface 330 with the contoured surface 331 as the flexible arm 429 moves distally.

Figure 5A:
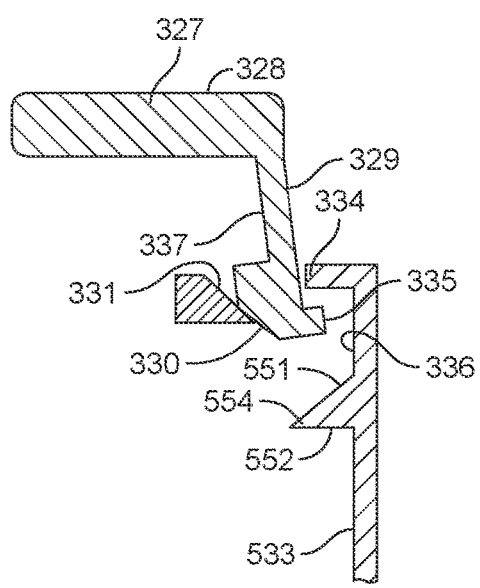
FIG. 5A is a schematic view of part of a medicament delivery device with the actuation member positioned between a first position and a second position and the blocking member in the retracted position.
Figure 5B:
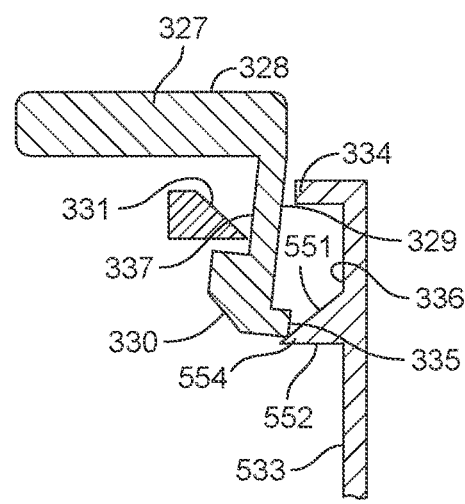
FIG. 5B is a schematic view of the part of the device of FIG. 5A with the actuation member located closer to the second position.
Figure 5C:
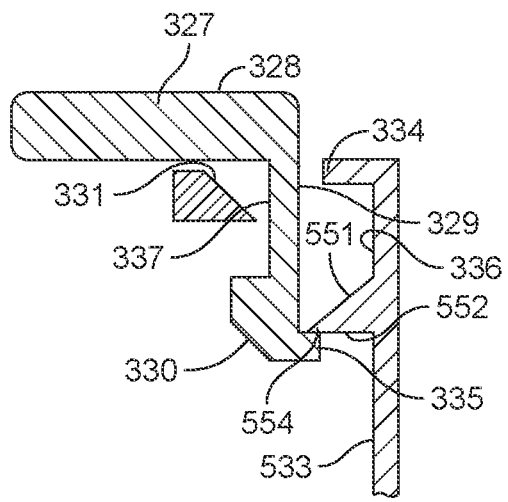
FIG. 5C is a schematic view of part of the device of FIG. 5A when the actuation member is in the second position.

FIGS. 5A to 5C show views of part of a medicament delivery device. The medicament delivery device of FIGS. 5A to 5C is similar to the medicament delivery device 300 described above, and has corresponding reference numerals for corresponding features. A difference of the embodiment of FIGS. 5A to 5C compared to the medicament delivery device 300 is that the blocking member 533 has a radially-extending protrusion 554 which has a contoured surface 551 configured to engage the flexible arm, such as by engaging the radially-extending protrusion 335 of the flexible arm, and radially deflect the flexible arm 329 when the actuation member 327 moves distally from the first position towards the second position as shown, for example, in FIG. 5B, when the blocking member is in the retracted position.

The radially-extending protrusion 554 is located distally from the contoured surface 331. The contoured surface 551 deflects the flexible arm 329 in the opposite direction to the deflection caused by the contoured surface 331. In the example of FIGS. 5A to 5C, the contoured surface 551 on the blocking member deflects the flexible arm 329 radially inwardly. In some embodiments, the contoured surface on the blocking member deflects the flexible arm radially outwardly.

The radially-extending protrusion 554 is located distally from the axially-extending recess 336 on the blocking member. The contoured surface 551 is planar. In some embodiments, the contoured surface 551 is curved and/or planar.

The radially-extending protrusion 554 on the blocking member has a locking surface 552 configured to engage the radially-extending protrusion 335 on the flexible arm 329 and to hold the blocking member 533 in the retracted position as shown, for example, in FIG. 5C. This reduces or prevents the hold force which a user is required to apply to maintain the blocking member 333 in the retracted position when the device is pressed against an injection site.

The contoured surface 551 is provided on a proximal side of the protrusion 554. The locking surface 552 is provided on a distal side of the protrusion 554.

In use, a user places the distal end of the blocking member 533 against an injection site to move the blocking member 533 from the extended position to the retracted position.

A user then presses the button 328 into the body. The flexible arm 329 is deflected radially by the engagement of the engagement surface 330 with the contoured surface 331 as the flexible arm 329 moves distally as shown, for example, in FIG. 5A.

The radially-extending protrusion 335 is at least partially received in the axially-extending recess 336 of the blocking member 533 when the flexible arm 329 is deflected radially by the contoured surface, and as the actuation member moves distally towards the second position.

When the engagement surface 330 moves distally past the contoured surface, the contoured surface 331 is at least partially received in the axially-extending recess 337 of the flexible arm to allow the flexible arm 329 to move radially towards an unflexed position.

The contoured surface 551 on the blocking member engages the flexible arm 329 and radially deflects the flexible arm 329 as the actuation member 329 moves distally. When the radially-extending protrusion 335 on the flexible arm moves distally past the contoured surface 551 on the blocking member, the flexible arm 329 moves radially towards the unflexed position. The radially-extending protrusion on the flexible arm engages the locking surface 552 to prevent the blocking member 533 from moving from the retracted position towards the extended position.

The blocking member 333 of FIGS. 3A to 3D and the blocking member 433 of FIG. 4 may be provided with a contoured surface 551 and a locking surface 552, as described above in relation to FIGS. 5A to 5C.

Figure 6:
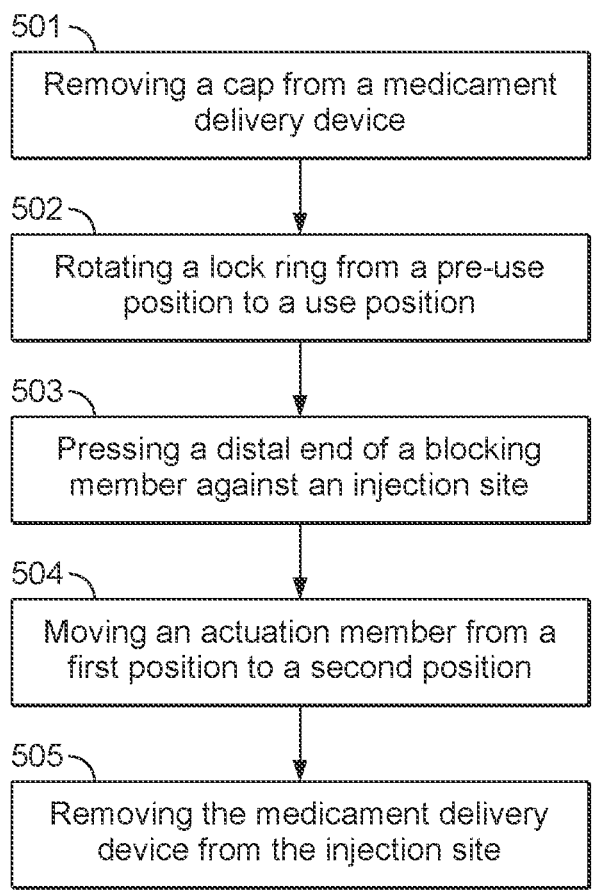
FIG. 6 is a flow chart of a method in accordance with one or more embodiments disclosed herein.

FIG. 6 is a flow chart of a method in accordance with one or more embodiments.

In a first step 501, the method includes removing a cap from the medicament delivery device. The medicament delivery device can have any of the features of the medicament delivery devices described herein.

In a subsequent step 502, the method includes rotating a lock ring from a pre-use position to a use position. In the pre-use position, the lock ring prevents movement of the actuation member from the first position towards the second position. In the use position, the lock ring permits movement of the actuation member from the first position towards the second position.

In a subsequent step 503, the method includes pressing a distal end of a blocking member against an injection site. Pressing the distal end of a blocking member against an injection site moves the blocking member relative to a body from an extended position to a retracted position.

In a subsequent step 504, the method includes moving an actuation member from a first position to a second position. Moving the actuation member from the first position to the second position activates a mechanism which automatically moves a needle from a pre-use position, in which the distal end of the needle is located within the body, to an injecting position in which the distal end of the needle protrudes outside of the body for injecting medicament.

In a subsequent step 505, the method includes removing the medicament delivery device from the injection site.

In some embodiments, the cap and hence method step 501 is optional. In some embodiments, the lock ring and hence method step 502 is optional. In some embodiments, the lock ring is rotated prior to or after the step 503 of pressing the distal end of the blocking member against the injection site.

LIST OF FEATURES

10—Device
11—housing
12—cap
13—needle sleeve
17—needle
20—distal region
21—proximal region
22—button
23—piston
200—medicament delivery device
201—body
202—distal end of the body
203—proximal end of the body
208—locking member
216—lock ring
217—needle
223—plunger
228—button
232—injection site
250—syringe
254—cap
260—spring
262—spring
300—medicament delivery device
301—body
302—distal end of the body
303—proximal end of the body
317—needle
318—distal end of needle
320—cap
323—plunger
327—actuation member
328—button
329—flexible arm
330—engagement surface
331—contoured surface
332—injection site 333—blocking member
334—proximal portion
335—radially-extending protrusion
336—axially-extending recess
337—axially-extending recess
338—locking surface
339—abutment surface
340—inner body
341—distal end of blocking member
342—protrusion
350—syringe
360—spring
362—spring
363—mechanism
364—clips
365—proximal opening
400—medicament delivery device
428—button
429—flexible arm
433—blocking member
434—proximal portion
435—radially-extending protrusion
501—method step
502—method step
503—method step
504—method step
505—method step
533—blocking member
551—contoured surface
552—locking surface
554—protrusion The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, proline in position B28 is replaced by Asp, Lys, Leu, Val or Ala and in position B29

Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful devices and methods disclosed herein include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

The invention claimed is:

1. A medicament delivery device comprising:
a body having a proximal end and a distal end;
a needle configured to be movable relative to the body from (i) an initial position in which a distal end of the needle is proximal to the distal end the body, to (ii) an injection position in which the distal end of the needle is distal to the distal end of the body for injecting a medicament;
an actuation member configured to be distally movable relative to the body from (i) a first position to (ii) a second position, the medicament delivery device being configured such that moving the actuation member relative to the body from the first position to the second position causes the needle to move from the initial position to the injection position, the actuation member comprising a flexible arm comprising an engagement surface;
a contoured surface configured to engage the engagement surface when the actuation member is in the first position, the medicament delivery device being configured such that when the actuation member moves distally from the first position to the second position, the flexible arm is deflected radially by the engagement of the engagement surface and the contoured surface; and
a blocking member configured to limit the movement of the actuation member from the first position to the second position, the blocking member being movable relative to the body between (i) an extended position in which a distal end of the blocking member is distal to the distal end of the body and (ii) a retracted position in which the blocking member is located proximally from the extended position,
wherein the blocking member comprises a proximal portion configured to engage the flexible arm when the blocking member is in the extended position and the actuation member is in the first position to limit distal movement of the flexible arm relative to the body by limiting the flexible arm from being deflected radially by the contoured surface, and
wherein the medicament delivery device is configured such that when the blocking member is in the retracted position, the proximal portion is disengaged from the flexible arm to allow the flexible arm to be deflected radially by the contoured surface as the flexible arm moves distally relative to the contoured surface while the contoured surface remains in a fixed position relative to the body.

2. The medicament delivery device of claim 1, wherein the flexible arm comprises a radially-extending protrusion configured to engage the proximal portion of the blocking member when the blocking member is in the extended position and the actuation member is in the first position.

3. The medicament delivery device of claim 2, wherein the blocking member comprises an axially-extending recess located distally from the proximal portion for at least partially receiving the radially-extending protrusion when the flexible arm is deflected radially by the contoured surface.

4. The medicament delivery device of claim 2, wherein the proximal portion of the blocking member is located radially outwardly of the radially-extending protrusion when the blocking member is in the extended position and the actuation member is in the first position.

5. The medicament delivery device of claim 2, wherein the proximal portion of the blocking member is located radially inwardly of the radially-extending protrusion when the blocking member is in the extended position and the actuation member is in the first position.

6. The medicament delivery device of claim 1, wherein the flexible arm comprises an axially-extending recess located proximal of the engagement surface for at least partially receiving the contoured surface to allow the flexible arm to move radially towards an unflexed position when the engagement surface moves distally beyond the contoured surface.

7. The medicament delivery device of claim 6, further comprising a locking surface, and the axially-extending recess of the flexible arm comprises an abutment surface configured to engage the locking surface for limiting proximal movement of the actuation member from the second position to the first position.

8. The medicament delivery device of claim 1, further comprising an inner body located within the body, the inner body comprising the contoured surface.

9. The medicament delivery device of claim 1, further comprising a biasing member for biasing the blocking member in a direction from the retracted position towards the extended position.

10. The medicament delivery device of claim 9, wherein the biasing member comprises a spring.

11. The medicament delivery device of claim 1, further comprising a cap removably attachable to the body, the cap configured to cover the distal end of the blocking member to limit the blocking member from being moved from the extended position to the retracted position when the cap is attached to the body.

12. The medicament delivery device of claim 1, wherein at least one of the contoured surface or the engagement surface comprises a planar surface.

13. The medicament delivery device of claim 1, wherein the contoured surface and the engagement surface comprise respective planar surfaces.

14. The medicament delivery device of claim 1, wherein at least one of the contoured surface or the engagement surface comprises a curved surface.

15. The medicament delivery device of claim 1, wherein the contoured surface and the engagement surface comprise respective curved surfaces.

16. The medicament delivery device of claim 1, further comprising a lock ring configured to rotate from (i) a first lock ring position in which the lock ring limits the movement of the actuation member from the first position to the second position to (ii) a second lock ring position in which the lock ring allows the movement of the actuation member from the first position to the second position.

17. The medicament delivery device of claim 1, wherein the blocking member comprises a radially-extending protrusion comprising a contoured surface configured to engage the flexible arm and radially deflect the flexible arm when the actuation member moves from the first position to the second position.

18. The medicament delivery device of claim 17, wherein the radially-extending protrusion of the blocking member comprises a locking surface configured to engage a radially-extending protrusion on the flexible arm and to hold the blocking member in the retracted position when the actuation member is in the second position.

19. The medicament delivery device of claim 1, wherein the actuation member comprises a button configured to be pressed by a user to move the actuation member from the first position to the second position, wherein at least a portion of the button protrudes from the body when the actuation member is in the first position.

20. The medicament delivery device of claim 19, wherein a proximal end of the button is proximal to the proximal end of the body when the actuation member is in the first position.

21. The medicament delivery device of claim 1, further comprising a syringe containing the medicament and comprising the needle.

22. The medicament delivery device of claim 1, further comprising a mechanism for automatically moving the needle from the initial position to the injection position.

23. The medicament delivery device of claim 22, wherein the mechanism comprises a plunger comprising one or more proximally-extending clips configured to releasably engage an inner body of the medicament delivery device to hold the plunger in a proximal position, the one or more proximally-extending clips configured to deflect radially by the actuation member to release the plunger from the proximal position when the actuation member is moved from the first position to the second position.

24. The medicament delivery device of claim 22, wherein the mechanism is configured such that moving the blocking member from the extended position to the retracted position does not activate the mechanism.

25. The medicament delivery device of claim 1, wherein the blocking member comprises a sleeve.

26. A medicament delivery device comprising:
a body;
a first member configured to be axially movable relative to the body, the first member comprising a first resilient arm;
a second member configured to be axially movable relative to the body, the second member comprising a second resilient arm;
a third member configured to be axially movable relative to the body, the third member configured to releasably engage the first resilient arm of the first member to releasably limit a a radial deflection of the first resilient arm relative to the third member and releasably limit a distal movement of the first member relative to the body; and
a fourth member comprising a contoured surface configured to releasably engage the first resilient arm of the first member to cause the first resilient arm to move into a recess of the third member and to allow the distal movement of the first member relative to the body,
wherein the medicament delivery device is configured such that the distal movement of the first member relative to the body (i) flexes the first resilient arm radially by the contoured surface while the contoured surface remains in a fixed position relative to the body and (ii) flexes the second resilient arm and causes a medicament to be dispensed from the medicament delivery device.

27. A method comprising:
pressing a distal end of a blocking member of a medicament delivery device against an injection site to move the blocking member relative to a body of the medicament delivery device from (i) an extended position in which distal movement of an actuation member of the medicament delivery device is limited due to a held engagement between one or more flexible arms of the actuation member and one or more contoured surfaces by the blocking member (ii) to a retracted position in which the distal movement of the actuation member is allowed due to the one or more flexible arms of the actuation member and the one or more contoured surfaces no longer being held in the engagement by the blocking member; and
when the blocking member is in the retracted position, moving the actuation member of the medicament delivery device from a first position to a second position such that the one or more flexible arms of the actuation member deflect radially by the one or more contoured surfaces while the one or more contoured surfaces remain in a fixed position relative to the body to activate a mechanism that automatically moves a needle from (i) an initial position in which a distal end of the needle is proximal to a distal end of the body to (ii) an injection position in which the distal end of the needle is distal to the distal end of the body for injecting a medicament.

28. The method of claim 27, comprising: when moving the actuation member from the first position to the second position, engaging the actuation member to a plunger to release the plunger from being held in a proximal position such that the plunger moves from the proximal position to a distal position against a biasing force of a spring.

29. A medicament delivery device comprising:
an outer body having a proximal end and a distal end;
an inner body disposed in the outer body, the inner body comprising one or more contoured surfaces located at a proximal end of the inner body, the inner body being configured to hold a medicament container containing a medicament;
a plunger comprising one or more proximally-extending clips releasably engaged to the inner body to hold the plunger in a first plunger position relative to the inner body;
a drive spring biasing the plunger in a distal direction relative to the inner body;
a member movably disposed relative to the outer body from a first member position to a second member position;
a button disposed at the proximal end of the outer body and configured to move from a a proximal button position to a distal button position, the button comprising
(i) one or more flexible arms configured to (a) be radially wedged between a proximal portion of the member and the one or more contoured surfaces of the inner body when the member is in the first member position to limit distal movement of the button from the proximal button position to the distal button position, and (b) deflect radially by the one or more contoured surfaces while the one or more contoured surfaces remain in a fixed position relative to the outer body when the member is in the second member position and the button is moved from the proximal button position to the distal button position; and (ii) one or more distally-extending protrusions configured to engage and deflect the one or more proximally-extending clips of the plunger to release the plunger from being held by the inner body when the button moves from the proximal button position to the distal button position to dispense the medicament from the medicament container when the medicament container is disposed in the medicament delivery device.

30. The medicament delivery device of claim 29, wherein the member comprises a sleeve slidably disposed relative to the outer body, the first member position is a distal sleeve position, and the second member position is a proximal sleeve position that is proximal to the distal sleeve position.

* * * * *

UNITED STATES PATENT AND TRADEMARK OFFICE
CERTIFICATE OF CORRECTION

| | | |
|---|---|---|
| PATENT NO. | : 12,337,160 B1 | Page 1 of 1 |
| APPLICATION NO. | : 18/640600 | |
| DATED | : June 24, 2025 | |
| INVENTOR(S) | : Alexander Hee-Hanson and Michael Parrott | |

It is certified that error appears in the above-identified patent and that said Letters Patent is hereby corrected as shown below:

In the Claims

Column 21, Line 30, Claim 1, after "end", insert -- of --

Column 23, Line 62, Claim 26, delete "a a" and insert -- a --

Column 24, Line 63, Claim 29, delete "a a" and insert -- a --

Column 24, Line 65, Claim 29, after "comprising", insert -- : --

Signed and Sealed this
Twelfth Day of August, 2025

Coke Morgan Stewart
*Acting Director of the United States Patent and Trademark Office*